United States Patent [19]

Cadiergue et al.

[11] Patent Number: 5,245,073
[45] Date of Patent: Sep. 14, 1993

[54] PROCESS FOR THE PREPARATION OF CERTAIN CYCLOPROPANE CARBOXYLATES

[75] Inventors: Joseph Cadiergue, Aulnay Sous Bois; Jean-Pierre Demoute, Montreuil-Sous-Bois; Jean Tessier, Vincennes, all of France

[73] Assignee: Roussel Uclaf, France

[21] Appl. No.: 747,702

[22] Filed: Aug. 20, 1991

Related U.S. Application Data

[62] Division of Ser. No. 423,803, Oct. 18, 1989, Pat. No. 5,082,832, which is a division of Ser. No. 123,374, Nov. 20, 1987, Pat. No. 4,925,874.

[30] Foreign Application Priority Data

Nov. 20, 1986 [FR] France .................. 86 16155

[51] Int. Cl.$^5$ ................ C07C 69/743; C07C 69/62; C07C 255/11
[52] U.S. Cl. .................. 560/124; 560/219; 558/52; 558/54; 558/168; 558/388; 558/407
[58] Field of Search ............ 560/124, 219; 558/407, 558/48, 54, 168, 388, 52

[56] References Cited

U.S. PATENT DOCUMENTS 4,551,281 11/1985 Crosby .................. 560/124 X

Primary Examiner—Alan L. Rotman
Attorney, Agent, or Firm—Bierman and Muserlian

[57] ABSTRACT

Novel 2,2-dimethyl-cyclopropane carboxylic acid derivatives of the formula

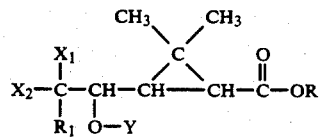

wherein $X_1$ and $X_2$ are individually halogen, $R_1$ is selected from the group consisting of halogen, alkyl of 1 to 8 carbon atoms, optionally substituted aryl of 6 to 14 carbon atoms, perfluoroalkyl of 1 to 8 carbon atoms, —CN and

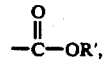

R' is alkyl of 1 to 8 carbon atoms, Y is selected from the group consisting of —SO$_2$Alk$_1$, —SO$_2$Ar,

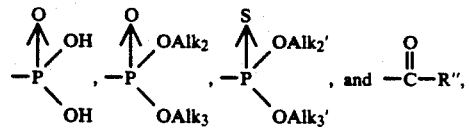

Alk$_1$ is optionally unsaturated alkyl of 1 to 8 carbon atoms optionally substituted with at least one halogen, Ar is aryl of 6 to 14 carbon atoms optionally substituted with at least one halogen, Alk$_2$ and Alk$_3$ and Alk$_2$' and Alk$_3$' are optionally unsaturated alkyl of up to 8 carbon atoms optionally substituted with at least one halogen or together with

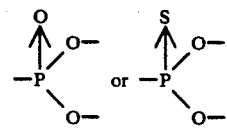

form the rings

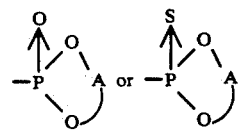

wherein A is optionally unsaturated alkyl of up to 6 carbon atoms optionally substituted with at least one halogen, R" is alkyl of 1 to 6 carbon atoms no substituted or substituted with at least one functional group or aryl of 6 to 14 carbon atoms no substituted or substituted with at least one functional group and R is selected from the group consisting of hydrogen, alkyl of 1 to 8 carbon atoms and residue of an alcohol used in pyrethrinoid esters having pesticidal activity.

3 Claims, No Drawings

PROCESS FOR THE PREPARATION OF CERTAIN CYCLOPROPANE CARBOXYLATES

PRIOR APPLICATION

This application is a division of U.S. patent application Ser. No. 423,803 filed Oct. 18, 1989, now U.S. Pat. No. 5,082,832 which is a division of U.S. patent application Ser. No. 123,374 filed Nov. 20, 1987, now U.S. Pat. No. 4,925,874.

STATE OF THE ART

Relevant prior art includes Chem. Abstract, Vol. 86, 139480a, Tetrahedron Letters, Vol. 27, No. 19, p. 2135 to 2138 and 2139 to 2142, European Patent No. 21,521, European Application 187,674 and German Patent Application Nr. 2,639,777 and British Patent Application Nr. 2,099,810.

OBJECTS OF THE INVENTION

It is an object of the invention to provide the novel compounds of formula I and a process for their preparation.

It is another object of the invention to provide the novel pesticidal compositions and a novel method of combatting pests.

These and other objects and advantages of the invention will become obvious from the following detailed description.

THE INVENTION

The novel compounds of the invention are compounds of the formula $$X_2-\underset{R_1}{\underset{|}{C}}-CH-\underset{O-Y}{\underset{|}{CH}}-\overset{CH_3}{\underset{}{\overset{|}{C}}}\overset{CH_3}{\underset{}{}}-CH-\overset{O}{\underset{}{\overset{\|}{C}}}-OR \quad I$$

wherein $X_1$ and $X_2$ are individually halogen, $R_1$ is selected from the group consisting of halogen, alkyl of 1 to 8 carbon atoms, optionally substituted aryl of 6 to 14 carbon atoms, perfluoroalkyl of 1 to 8 carbon atoms, —CN and $$-\overset{O}{\underset{}{\overset{\|}{C}}}-OR',$$

R' is alkyl of 1 to 8 carbon atoms, Y is selected from the group consisting of —SO$_2$Alk$_1$, —SO$_2$Ar, $$-P\overset{O}{\underset{OH}{\diagdown}}\overset{\nearrow OH}{\diagup}, -P\overset{O}{\underset{OAlk_3}{\diagdown}}\overset{\nearrow OAlk_2}{\diagup}, -P\overset{S}{\underset{OAlk_3'}{\diagdown}}\overset{\nearrow OAlk_2'}{\diagup}, \text{ and } -\overset{O}{\underset{}{\overset{\|}{C}}}-R'',$$

Alk$_1$ is optionally unsaturated alkyl of 1 to 8 carbon atoms no substituted or substituted with at least one functional group, Ar is aryl of 6 to 14 carbon atoms no substituted or substituted with at least one functional group, Alk$_2$ and Alk$_3$ and Alk$_{2'}$ and Alk$_{3'}$ are optionally unsaturated alkyl of 1 to 8 carbon atoms no substituted or substituted with at least one functional group or together with $$-P\overset{O}{\underset{O-}{\diagdown}}\overset{\nearrow O-}{\diagup} \text{ or } -P\overset{S}{\underset{O-}{\diagdown}}\overset{\nearrow O-}{\diagup}.$$

form the rings $$-P\overset{O}{\underset{O}{\diagdown}}\overset{\nearrow O\diagdown}{\diagup}A \text{ or } -P\overset{S}{\underset{O}{\diagdown}}\overset{\nearrow O\diagdown}{\diagup}A$$

wherein A is optionally unsaturated alkyl of 1 to 6 carbon atoms optionally substituted with at least one functional group, R" is alkyl of 1 to 6 carbon atoms no substituted or substituted with at least one functional group or aryl of 6 to 14 carbon atoms no substituted or substituted with at least one functional group and R is selected from the group consisting of hydrogen, alkyl of 1 to 8 carbon atoms and residue of an alcohol used in pyrathrinoid esters.

The compounds of formula I have several centers of asymmetry, the carbons in positions 1 and 3 of cyclopropane and the carbons in positions 1' and 2' of the $$\text{lateral chain } -\underset{OY}{\underset{|}{CH}}\overset{(1')}{-}\underset{R_1}{\overset{(2')}{\underset{|}{C}}}\overset{X_1}{\underset{\diagdown X_2}{\diagup}}$$

can also present several centers of asymmetry in part R. The subject of the invention is the various possible stereoisomers as well as mixtures of these stereoisomers.

Examples of $X_1$ and $X_2$ are chlorine, bromine and iodine and examples of $R_1$ are halogen such as bromine, chlorine or fluorine, alkyl such as methyl, ethyl, isopropyl, n-propyl, n-butyl, isobutyl and tert-buty, aryl such as phenyl, substituted aryl such as phenyl substituted with a halogen such as chlorine, perfluoroalkyl such as trifluoromethyl and $$-\overset{O}{\underset{}{\overset{\|}{C}}}-OR'$$

where R' is methyl, ethyl, n-propyl, isopropyl, tert.-butyl or hexafluoroisopropyl.

Examples of preferred groups of $X_1$, X and $R_1$ are $$\underset{Cl}{\overset{Cl}{\diagdown}}\overset{\diagup Hal_1}{C\diagdown} \quad \text{with Hal}_1 = \text{Br, I}$$

$$\underset{Br}{\overset{Br}{\diagdown}}\overset{\diagup Hal_2}{C\diagdown} \quad \text{with Hal}_2 = \text{Br, I}$$

$$\underset{CF_3}{\overset{Cl}{\diagdown}}\overset{\diagup Hal_3}{C\diagdown} \quad \text{with Hal}_3 = \text{Br, I}$$

-continued

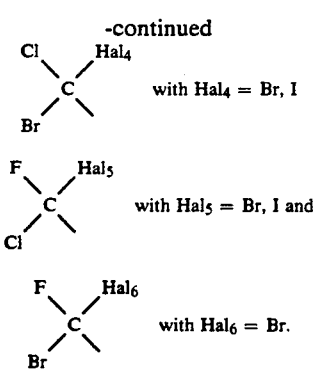

Alk$_1$, Alk$_2$, Alk$_3$, Alk$_2'$ and Alk$_3'$ preferably are methyl, ethyl, n-propyl, isopropyl, n-butyl, isobutyl or t-butyl Ar preferably is phenyl.

When Alk$_1$, Alk$_2$, Alk$_3$, Alk$_2'$, Alk$_3'$ and Ar are substituted, the substituent is preferably at least one of halogen, —CF$_3$, hydroxyl, carboxyl, amino, and ammonium, alkyl and alkoxy of 1 to 4 carbon atoms such as methyl and methoxy.

Examples of R″ are methyl, ethyl, propyl, phenyl, each optionally substituted with halogen.

A preferably is a saturated carbonated chain of 1 to 4 carbon atoms, optionally substituted by at least one member selected from the group consisting of alkyl of 1 to 5 carbon atoms, halogen, —CF$_3$ or hydroxyl. When R is alkyl, it is preferably methyl, ethyl, n-propyl, isopropyl, butyl, isobutyl or tert-butyl.

The preferred values of the alcohols used in the synthesis of pyrethrinoid esters will be indicated hereafter.

Among the preferred compounds of formula I are those wherein X$_1$ and X$_2$ are bromine, those wherein R$_1$ is bromine, chlorine or fluorine and those wherein R$_1$ is —CF$_3$. Other preferred compounds of formula I are those wherein Y is —SO$_2$Alk$_1$ and Alk$_1$ is alkyl or alkenyl of up to 8 carbon atoms, for example SO$_2$CH$_3$, those wherein Y is SO$_2$Ar, Ar having the same significance as previously, as well as compounds of formula I in which R is hydrogen, or optionally substituted alkyl of 1 to 8 carbon atoms, or benzyl optionally substituted by a member chosen from the group constituted of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogen, or

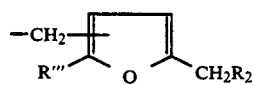

in which R‴ is hydrogen or methyl and R$_2$ is a monocyclic aryl or a —CH$_2$=CH group and particularly 5-benzyl-3-furyl, methyl, or

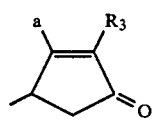

in which a is hydrogen or methyl and R$_3$ is aliphatic organic radical of 2 to 6 carbon atoms and containing at least one carbon-carbon unsaturation and particularly one of the following —CH$_2$—CH=CH$_2$, —CH=CH—CH$_3$, —CH$_2$—CH=CH—CH=CH$_2$, —CH$_2$—CH=CH—CH$_2$—CH$_3$, —CH$_2$—C≡CH, or

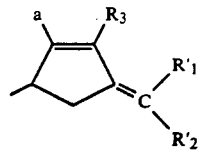

in which a is hydrogen or methyl, R$_3$ has the above definition, R$_1'$ and R$_2'$ are individually hydrogen, halogen, alkyl of 1 to 6 carbon atoms, aryl of 6 to 10 carbon atoms, alkyloxycarbonyl of 2 to 5 carbon atoms, or cyano, or

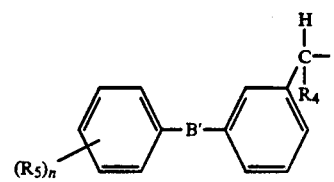

in which B′ is oxygen or sulfur,

or —CH$_2$— or a sulfoxide or a sulfone and R$_4$ is hydrogen, —C≡N, methyl, —CONH$_2$, —CSNH$_2$, or —C≡CH, R$_5$ is halogen or methyl and n is a number equal to 0, 1 or 2, and particularly one of the following groups: 3-phenoxy-benzyl, α-cyano-3-phenoxy-benzyl, α-ethynyl-3-phenoxy-benzyl, 3-benzoyl-benzyl, 1-(3-phenoxy-phenyl)-ethyl or α-thioamido-3-phenoxy-benzyl, or

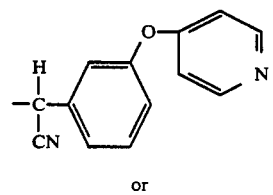

or

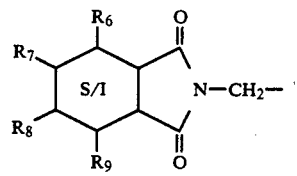

in which the substituents R$_6$, R$_7$, R$_8$ and R$_9$ are hydrogen, chlorine, or methyl and in which S/I symbolizes an aromatic ring or a similar dihydro or tetrahydro ring, or

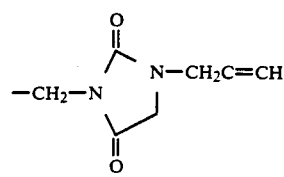

-continued
or

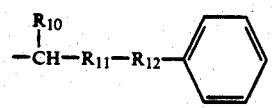

in which $R_{10}$ is hydrogen or —CN, $R_{12}$ is —CH$_2$— or oxygen, $R_{11}$ is thiazolyl or thiadiazolyl of which the bond with

can be found at any one of the available positions, $R_{12}$ being linked to $R_{11}$ by the carbon atom included between the sulfur atom and a nitrogen atom, or

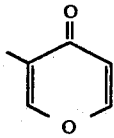

or

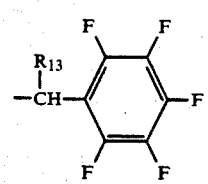

in which $R_{13}$ is hydrogen or —CN, or

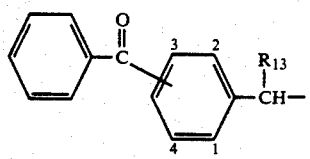

in which $R_{13}$ is defined as above, and benzoyl is in position 3 or 4, or

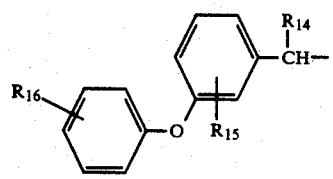

in which $R_{14}$ is hydrogen, methyl, ethynyl or cyano and $R_{15}$ and $R_{16}$, being different, is hydrogen, fluorine or bromine, or

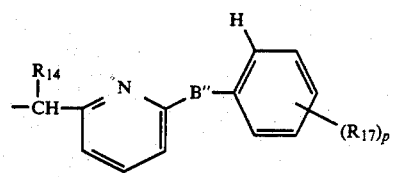

in which $R_{14}$ is defined as above, each $R_{17}$ is independently alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo, p is a number equal to 0, 1 or 2 and B'' is oxygen or sulfur, or

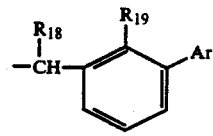

in which $R_{18}$ is hydrogen, methyl, ethynyl, or cyano and $R_{19}$, being different, is hydrogen, fluorine or bromine and Ar is aryl of 6 to 14 carbon atoms, or

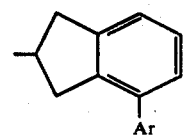

or

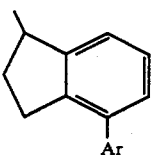

Among the preferred compounds of formula I are compounds in which R is one of the following:

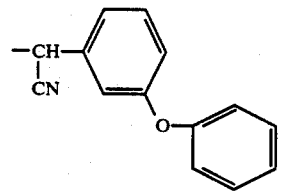

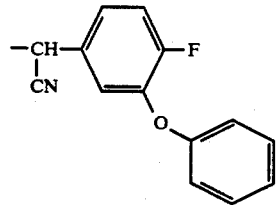

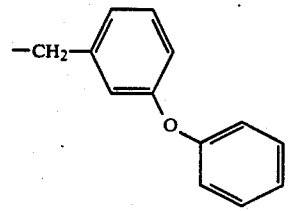

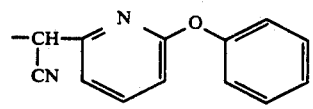

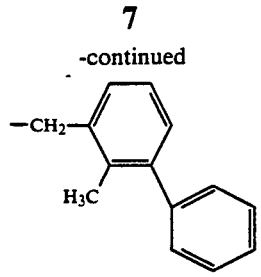

Among the preferred compounds of formula I: α-cyano-3-phenoxy-benzyl 1R-[1α-(S) 3α-(R)]2,2-dimethyl-3-[1-(methylsulfonyloxy ethyl)-2,2,2-tribromoethyl]-cyclopropane carboxylate α-cyano-3-phenoxy-benzyl 1R-[1α-(S) 3α-(R)]2,2-dimethyl-3-[3-[2,2,2-tribromo-1-methylsulfonyloxyethyl]-cyclopropane carboxylate, α-cyano-3-phenoxy-4-fluoro-benzyl 1R-[1α-(S) 3α-(R)]2,2-dimethyl-3-[2,2,2-tribromo-1-methylsulfonyloxyethyl]-cyclopropane carboxylate, [2-methyl-3-phenylbenzyl]1R-[1α,3α-(RS,RS)]2,2-dimethyl-3-[2-trifluoromethyl-2-bromo-2-chloro-1-methylsulfonyloxyethyl]-cyclopropane carboxylate and α-cyano-3-phenoxy-benzyl 1R-[1α-, 3α-(RS*,RS*)]2,2-dimethyl-3-[2 trifluoromethyl-2-bromo-2-chloro-1-methysulfonyloxyethyl]-cyclopropane carboxylate.

The novel process of the invention for the preparation of the compounds of formula I comprises reacting a compound of the formula

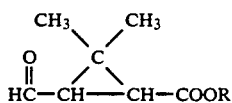    II wherein R has the above definitions with a compound of the formula

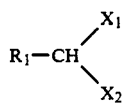    V wherein R₁, X₁ and X₂ have the above definitions in the presence of a base to obtain a compound of the formula

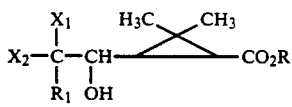    IV submitting the latter to the action of a sulfonylation, phosphonylation, thiophosphorylation or acylation agent to obtain a compound of the formula

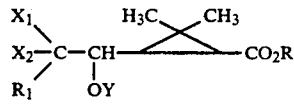    I which is optionally changed into the corresponding acid which is optionally reacted with an esterification agent to obtain another compound of formula I.

In a preferred method of the process of the invention, the base used for reaction of the compound of formula II with the compound of formula V is preferably selected from the group consisting of alkali metal alcoholates, alkali metal hydrides and alkali metal hydroxides, preferably potassium hydroxide, potassium methylate or potassium tertbutylate.

The sulfonylation agent may have the formula

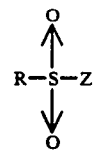

with Z being halogen, O—PO₃—Alk—OSO₂Alk or imidazolyl and Alk is alkyl of 1 to 8 carbon atoms, the phosphorylation agent may have the formula

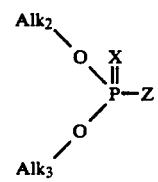

with Z being halogen, —OSO₂R or imidazolyl
X is oxygen or sulfur and Alk₂ and Alk₃ have the above definitions and the acylation agent may have the formula

with Z being —OCOAlk, halogen,

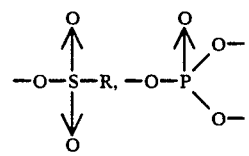

or imidazolyl,

The agent of formula I can be prepared by reacting an ester of formula I with an acid hydrolysis agent, for example p-toluenesulfonic acid, sulfuric acid or acetic acid and the esterification agent is an alcohol with esterification being carried out according to standard methods.

The products of formula IV obtained by the process are new products with the exception of products for which X₁, X₂ and R₁ each is halogen.

The novel pesticidal compositions of the invention are comprised of a pesticidally effective amount of at least one stereoisomer or mixtures thereof of formula I and an inert carrier. The compositions are useful for combatting vegetation parasites, premises parasites and warm-blooded animals parasites and are useful particularly to combat insects, nematodes and vegetation and animal acariens.

In compositions intended for agricultural use and for use in premises, the active compounds of formula I may have added to them one or more other pesticide agents and these compositions may be in the form of powders, granules, suspensions, emulsions, solutions, solutions for aerosols, combustible strips, baits or other preprations normally employed for the utilization of this type of compound.

In addition to the active principle, the compositions generally contain a vehicle and/or a non-ionic surface active agent to ensure a uniform dispersion of the substances which form the mixture. The vehicle utilized can be a liquid such as water, alcohol, hydrocarbons or other organic solvents, a mineral, animal or vegetable oil, a powder such as talc, clays, silicates, kieselguhr or a combustible solid.

The products of formula I can be used particularly to combat insects in the agricultural field, to combat, for example, aphids, larvae of lepidoptera and coleoptera. They are used at doses between 10 g and 300 g of active material per hectare. The products of formula I can also be used to combat premises insects, to combat particularly flies, mosquitoes and cockroaches. The products of formula I may also be used to combat parasitic insects of animals, for example, lice, particularly on cattle, sheep and fowls.

The invention also has particularly as its object insecticide compositions containing as active principle at least one of the compounds previously defined. The preferred insecticidal compositions contain as active principle α-cyano-3-phenoxy-benzyl 1R-[1α-(S) 3α-(R)]2,2-dimethyl-3-[1-methylsulfonyloxy ethyl]-2,2,2-tribromoethyl]-cyclopropane carboxylate α-cyano-3-phenoxy-benzyl, 1R-[1α-(S) 3α-(R)]2,2-dimethyl -3-[3-[2,2,2-tribromo-1-methylsulfonyloxyethyl]-cyclopropane carboxylate, α-cyano-3-phenoxy-4-fluoro-benzyl 1R-[1α-(S) 3α-(R)]2,2-dimethyl-3-[2,2,2-tribromo-1-methylsulfonyloxyethyl]-cyclopropane carboxylate, [2-methyl-3-phenyl-benzyl]1R-[1α, 3α-(RS,RS) ]2,2-dimethyl-3-[2-trifluoromethyl-2-bromo-2-chloro-1-methylsulfonyloxyethyl]-cyclopropane carboxylate and a α-cyano-3-phenoxy-benzyl 1R-[1α-, 3α-(RS*,RS*)]2,2-dimethyl-3-[2trifluoromethyl-2-bromo-2-chloro-1-methylsulfonyloxyethyl]-cyclopropane carboxylate. The insecticidal compositions of the invention preferably contain from 0.005% to 10% by weight of active material.

According to an advantageous way of operating, for use in premises, the insecticide compositions of the invention are utilized in the form of fumigating compositions. The insecticide compositions of the invention may then be constituted advantageously, for the non-active part, of a combustible serpentine or of an incombustible fibrous substrate. In this latter case, the fumigant obtained after incorporation of the active material is placed on a heating apparatus such as an electroemanator. If an insecticide serpentina is used, the inert support can be, for example, composed of pyrethrum marc, Tabu powder (or Machilus Thunbergii leaf powder), pyrethrum stem powder, cedar leaf powder, wood powder (such as pine sawdust), starch and coconut shell powder. The quantity of active material can then be, for example, from 0.03 to 1% by weight. If an incombustible fibrous support is used, the quantity of active material can then be, for example, from 0.03 to 95% by weight.

The compositions of the invention for use in premises can also be obtained by preparing an atomizable oil based on the active principle, this oil soaking the wick of a lamp and then being submitted to combustion. The concentration of active principle incorporated in the oil is preferably from 0.03 to 95% by weight.

The invention compounds can also be used to combat parasitic acariens of vegetation and the biological study further on clearly shows the remarkable acaricide properties of the products. The compositions may also be used to combat parasitic nematodes of vegetation. Therefore, the invention also has as its object acaricide compositions as well as nematocide compositions containing as active prinicple at least one compound of formula I. The acaricide and nematocide compositions can be presented in particular in the form of powders, granules, suspensions, emulsions, and solutions.

For acaricide use, it is preferred to use wettable powders for foliar atomization containing from 1 to 80% of active principle, or liquids for foliar atomization containing from 1 to 500 g/l of active material. Powders for foliar powdering can also be used containing from 0.05 to 3% of active material. For nematocide use, it is preferred to use liquids for soil treatment containing from 300 to 500 g/l of active principle. The araricide and nematocide compounds of the invention are used preferably at quantities between 1 and 100 g of active material per hectare.

The compounds of formula I can also be used to combat parasitic acariens of animals such as ticks and particularly ticks of the Boophilus species, those of the Hyalomnia species, those of the Amblyomnia species and those of the Rhipicephalus species, or to combat all sorts of mites and particularly sarcoptic mites, psoroptic mites and chorioptic mites. Therefore, the invention also has as its subject compositions used in combatting parasitic acariens of warm-blooded animals, characterized in that they contain at least one product defined above.

Those compositions can be administered externally by vaporizing, by shampooing, by bath, or by painting on. They can also be administered by painting on the backbone by the so-called "pour on" method and they can also be administered by the digestive route.

When it is a matter of combatting parasitic acariens of animals, the compositions are very often incorporated in alimentary compositions in association with a nutritive mixture suitable for feeding the animal which nutritive mixture vary according to the animal species. It can contain cereals, sugars and seeds, soya, ground-nut and sunflower cakes, meals of animal origin, for example, fish meals, synthetic amino acids, mineral salts, vitamins and anti-oxidants. Thus, the invention also has as its object compositions intended for animal feeding containing as active principle at least one of the products of formula I.

To increase the biological activity of the products of the invention, they can have added to them standard synergists used in similar cases such as 1-(2,5,8-trioxadodecyl)-2-propyl-4,5-methylenedioxy benzene (or piperonyl butoxide) or N-(2-ethylheptyl)-bicyclo[2,2,1]-5-hepten-2,3-dicarboximide, or piperonyl-bis-2-(2'n-butoxyethoxy)-ethyl-acetal (or tropital).

The invention also has as its object compositions endowed with insecticide, acaricide or nematocide activity characterized in that they contain as active material, on the one hand, at least one of the compounds of formula I, and on the other hand, at least one of the pyrethrinoid esters selected from the group consisting of esters of allethrolones, of 3,4,5,6-tetrahydrophthalimidomethyl alcohol, of 5-benzyl-3-furyl methyl alcohol, of 3-phenoxy-benzyl alcohol and α-cyano-3-phenoxy-benzyl alcohols with chrysanthemic acids, by the esters of 5-benzyl-3-furyl methyl alcohol with 2,2-dimethyl-3-(2-oxo-3-tetrahydrothiophenylidenemethyl)-cyclopropane-1-carboxylic acids, by the esters of 3-phenoxy-benzyl alcohol and α-cyano-3-phenoxy-benzyl alcohols with 2,2-dimethyl-3-(2,2-dichlorovinyl)- cyclopropane-1-carboxylic acids, by the esters of α-cyano-3-phenoxy-benzyl alcohols with 2,2-dimethyl-3-(2,2-dibromovinyl)-cyclopropane-1-carboxylic acids, by the esters of 3-phenoxy-benzyl alcohol with 2-parachlorophenyl-2-isopropyl acetic acids, by the esters of allethrolone, 3,4,5,6-tetrahydrophthalimidomethyl alcohol, of 5-benzyl-3-furyl-methyl alcohol, of 3-phenoxy-benzyl alcohol and α-cyano-3-phenoxy-benzyl alcohols with 2,2-dimethyl-3-(1,2,2,2-tetrahaloethyl)-cyclopropane-1-carboxylic acids, in which "halo" represents a fluorine, chlorine or bromine atom, it being understood that the compounds I can exist in all their possible stereo-isomeric forms, as can the acid and alcohol moiety of the above pyrethrinoid esters. The said compositions are of particular interest because of their wider range of parasitic activity due to the polyvalency of their action and having a synergistic effect in some instances.

The compounds of formula I may also be used to prepare a compound of the formula

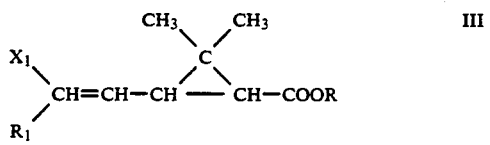

by reacting a compound of formula I with a reducing agent. The preferred reducing agent is hydrogen in the presence of a hydrogenation catalyst such as palladium but reduction can also be effected with zinc in the presence of an acid or with copper-zinc in the presence of an alcohol or any other conventional method for simultaneous removal of a halogen and -OY.

The preferred compounds of formula III which may be produced by the above process starting from the corresponding compounds of formula I have the formulae

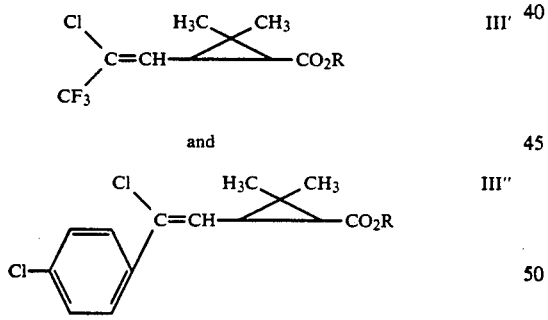

In the following examples there are described several preferred embodiments to illustrate the invention. However, it should be understood that the invention is not intended to be limited to the specific embodiments.

EXAMPLE 1

α-Cyano-3-phenoxy-benzyl 1R-[1α-(S) 3α-(R)] 2,2-dimethyl-3-(1-hydroxy-2,2,2-tribromoethyl)-cyclopropane carboxylate STEP A: 1R-[1α,3α-(R)] 2,2-dimethyl-3-[1-trimethylsilyloxy) 2,2,2-tribromoethyl]-cyclopropane carboxylic acid 18.5 g of potassium tertbutylate, 40 ml of tetrahydrofuran and 80 ml of tertbutyl alcohol were introduced at −60° C. over 30 minutes into a solution containing 30.25 g of 1R-[1α,-3α-(R) 2,2-dimethyl-3-[1-hydroxy-2,2,2-tribromoethyl]-cyclopropane carboxylic acid [described in French Patent No. 2,396,006] and 300 ml of tetrahydrofuran. The mixture was stirred for 10 minutes at −60° C. and 80 ml of trimethylsilyl chloride and 60 ml of tetrahydrofuran were introduced dropwise. The mixture was stirred for 10 minutes at −60° C. and the ambient temperature was allowed to rise to −20° C. Then, stirring was carried out for half an hour at −20° C. and the reaction mixture was poured into a saturated solution of sodium bicarbonate. Extraction was carried out with chloroform and the extracts were dried and evaporated to dryness under reduced pressure. 100 ml of water with 1% of acetic acid were added and the mixture was stirred for 15 minutes. The product obtained was separated, dissolved in chloroform, dried and evaporated to dryness under reduced pressure to obtain 16 g of 1R-[1α,3α-(R)] 2,2-dimethyl-3-[1-trimethylsilyloxy) 2,2,2-tribromoethyl]-cyclopropane carboxylic acid melting at 147° C.

STEP B: α-Cyano-3-phenoxyl-benzyl 1R-[1α-(S) 3α-(R) 2,2-dimethyl-3-[1-trimethylsilyloxy]-2,2,2-tribromoethyl]-cyclopropane carboxylate A solution of 14 g of dicyclohexylcarbodiimide and 140 ml of methylene chloride were introduced into a solution of 32 g of the product of Step A, 300 ml of methylene chloride and 15 g of (S)α-cyano-3-phenoxybenzyl alcohol. The mixture was stirred for 3 hours at 20° C. to 25° C., then separated and evaporated to dryness under reduced pressure. Purification was carried out by chromatography, elution with a hexane-isopropyl ether mixture (8-2) to obtain 34 g of α-cyano-3-phenoxy-benzyl 1R-[1α-(S) 3α-(R) 2,2-dimethyl-3-[1-trimethylsilyloxy)-2,2,2-tribromoethyl]-cyclopropane carboxylate melting at 98° C.

STEP C: α-Cyano-3-phenoxy-benzyl 1R-[1α-(S) 3α-(R) 2,2-dimethyl-3-(1-hydroxy-2,2,2-tribromoethyl)-cyclopropane] carboxylate 3 ml of 2N hydrochloric acid were added to a solution of 8 g of the product of Step B and 150 ml of methanol and after stirring for 30 minutes at 20° C. to 25° C., the methanol was expelled. The remainder was taken up in methylene chloride, dried and evaporated to dryness under reduced pressure. The residue was chromatographed over a medium eluting with a hexane-ethyl acetate mixture (7-3) to obtain 6.5 g of α-cyano-3-phenoxy-benzyl 1R-[1α-(S) 3α-(R) 2,2-dimethyl-3-[1-trimethylsiloxyl)-2,2,2-tribromoethyl]-cyclopropane carboxylate.

NMR Spectrum CDCl3 ppm

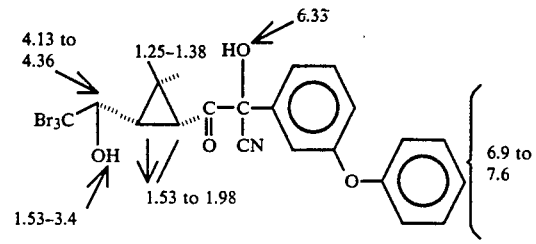

EXAMPLE 2

α-Cyano-3-phenoxy-benzyl 1R-[1α-(S) 3α-(R)] 2,2-dimethyl-3-[1-(methylsulfonyloxyethyl)-2,2,2-tribromoethyl]-cyclopropane carboxylate 0.91 ml of triethylamine were introduced at 0° to 5° C. into a mixture of 3 g of the product of Example 1, 30 ml of tetrahydrofuran and 0.5 ml of mesyl chloride and the mixture was stirred for 2 hours at 0° to 5° C. 0.5 ml of mesyl chloride and 0.91 ml of triethylamine were added again and the precipitate formed was separated. The organic phase was washed with water, dried and evaporated to dryness under reduced pressure. Chromatography was done on silica and elution with a hexane-ethyl acetate mixture (7-3) yielded 2.6 g of α-cyano-3-phenoxy-benzyl 1R-[1α-(S) 3α-(R)] 2,2-dimethyl-3-[1-(methylsulfonyloxy)-2,2,2-tribromoethyl]-cyclopropane carboxylate.

NMR Spectrum CDCl$_3$ ppm

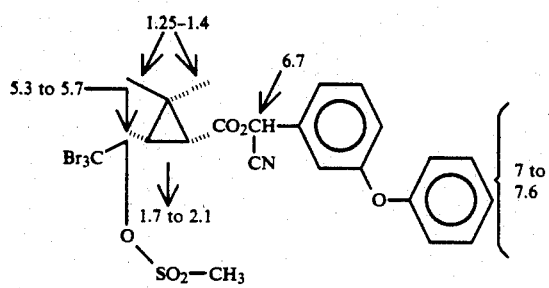

EXAMPLE 3

α-Cyano-3-phenoxy-benzyl 1R-[1α-(S*) 3α-(R*)] 2,2-dimethyl-3-(2,2,2-tribromo-1-ethyl-sulfonyloxyethyl)-cyclopropane carboxylate Using the procedure of Example 2, the product of Example 1 and ethane sulfonyl chloride were reacted to obtain α-cyano-3-phenoxy-benzyl 1R-[1α-(S*) 3α-(R*)] 2,2-dimethyl-3-(2,2,2-tribromo-1-ethyl-sulfonyloxyethyl)-cyclopropane carboxylate melting at 133° C. and having a specific rotation of $[\alpha]_D^{20} = +43°$ (c=1% in CHCl$_3$).

EXAMPLE 4

α-Cyano-3-phenoxy-benzyl 1R-[1α-(S) 3α-(R)] 3-(2,2,2-tribromo-1-isopropyl sulfonyloxy-ethyl)-2,2-dimethyl-cyclopropane carboxylate 0.35 ml of triethylamine were introduced at a temperature of 0° to 5° C. into a solution of 1.5 g of the product of Example 1, 15 ml of tetrahydrofuran and 0.32 g of isopropylsulfonyl chloride and the mixture was stirred at 0° to 5° C. for 30 minutes. The reaction mixture was poured into an aqueous solution of hydrochloric acid at pH 5 and then was extracted with methylene chloride. The extracts were dried, filtered and evaporated to dryness. 1.5 g of p-nitroperbenzoic acid were introduced and the mixture was stirred for 30 minutes at 20° to 25° C. and evaporated to dryness to obtain 3.2 g of crude product which was chromatographed over silica and eluted with a hexane-acetic acid (8-2) mixture to obtain 1.43 g of α-cyano-3-phenoxy-benzyl 1R-[1α-(S) 3α-(R)] 3-(2,2,2-tribromo-1-isopropyl sulfonyloxyethyl]-2,2-dimethyl-cyclopropane carboxylate with a specific rotation of $[\alpha]_D^{20} = +42°\pm1.5$ (c=0.7% in CHCl$_3$).

EXAMPLE 5

α-Cyano-3-phenoxy-benzyl 1R-[1α-(S) 3α-(R)] 3-[2,2,2-tribromo-1-(2-methyl-2-propene-1-sulfonyloxyethyl]-2,2-dimethyl-cyclopropane carboxylate Using the procedure of Example 2, the product of Example 1 and (1-sulfonyloxy-2-methyl)-2-propenyl chloride were reacted to obtain α-cyano-3-phenoxy-benzyl 1R-[1α-(S) 3α-(R)] 3-[2,2,2-tribromo-1-(2-methyl-2-propene-1-sulfonyloxyethyl]-2,2-dimethyl-cyclopropane carboxylate melting at 107° C.

EXAMPLE 6

α-(R,S) cyano 1-(6-phenoxy-2-pyridyl)-methyl 1R-[1α-(R,S) 3α-(R)] 2,2-dimethyl-3-[2,2,2-tribromo-1-methylsulfonyloxyethyl]-cyclopropane carboxylate

STEP A: α-(R,S) cyano 1-(6-phenoxy-2-pyridyl)-methyl 1R-[1α-(R,S) cyano 1-(6-phenoxy-2-pyridyl)-methyl 1R-[1α-(R,S) 3α-(R*)] 2,2-dimethyl-3-[2,2,2-tribromo-1-trimethylsilyloxyethyl]-cyclopropane carboxylate Using the procedure of Step B of Example 1, 1R-[1α-3α-(R)] 2,2-dimethyl-3-[trimethylsilyloxy-2,2,2-tribromoethyl]-cyclopropane carboxylic acid and α-(R,S) cyano 1-(6-phenoxy-2-pyridyl)-methyl alcohol were reacted to obtain α-(R,S) cyano 1-(6-phenoxy-2-pyridyl)-methyl 1R-[1α(R,S) cyano 1-(6-phenoxy-2-pyridyl)-methyl 1R-[1α-(R,S) 3α-(R*)] 2,2-dimethyl-3-[2,2,2-tribromo-1-trimethylsilyloxyethyl]-cyclopropane carboxylate melting at 160° C.

STEP B: α-(R,S) cyano-1-(6-phenoxy-2-pyridyl)-methyl 1R-[1α-(R,S) 3α-(R*)] 2,2-dimethyl-3-[2,2,2-tribromo-1-methylsulfonyloxyethyl]-cyclopropane carboxylate Using the procedure of Example 1, the product of Step A was reacted to obtain α-(R,S) cyano-1-(6-phenoxy-2-pyridyl)-methyl 1R-[1α-(R,S) 3α-(R*)] 2,2-dimethyl-3-[2,2,2-tribromo-1-methylsulfonyloxyethyl]-cyclopropane carboxylate which was used as is in the next step.

STEP C: α-(R,S) cyano 1-(6-phenoxy-2-pyridyl)-methyl 1R-[1α-(R,S) 3α-(R*)] 2,2-dimethyl 3-[2,2,2-tribromo-1-methylsulfonyloxyethyl]-cyclopropane carboxylate Using the procedure of Example 2, the product of Step B and mesyl chloride were reacted to obtain α-(R,S) cyano 1-(6-phenoxy-2-pyridyl)-methyl 1R-[1α-(R,S) 3α-(R*)] 2,2-dimethyl 3-[2,2,2-tribromo-1-methylsulfonyloxyethyl]-cyclopropane carboxylate with a specific rotation of $[\alpha]_D^{20} = +6°\pm1.5°$ (c=0.3% in CHCl$_3$).

EXAMPLE 7

3-phenoxy-benzyl 1R-[1α-,3α-(R)]2,2-dimethyl-3-(2,2,2-tribromo-1-methylsulfonyloxyethyl)-cyclopropane carboxylate STEP A: 3-phenoxy-benzyl 1R-[1α-, 3α-(R)] 2,2-dimethyl-3-(2,2,2-tribromo-1-trimethylsilyloxyethyl)-cyclopropane carboxylate Using the procedure of Example 6, the product of Step A of Example 1 and phenoxy-benzyl alcohol were reacted to obtain 3-phenoxybenzyl 1R-[1α, 3α(R)] 2,2-dimethyl-3-(2,2,2-tribromo-1-trimethylsilyloxyethyl)-cyclopropane carboxylate.

STEP B: 3-phenoxy-benzyl 1R-[1α-, 3α-(R*)] 2,2-dimethyl-3-(2,2,2-tribromo-1-hydroxyethyl)-cyclopropane carboxylate Using the procedure of Step B of Example 6, the product of Step A was reacted to obtain 3-phenoxybenzyl 1R-[1α, 3α(R*)] 2,2-dimethyl-3-(2,2,2-tribromo-1-hydroxyethyl)-cyclopropane carboxylate which was used as is in the next step.

STEP C: 3-phenoxy-benzyl 1R-[1α-, 3α-(R)] 2,2-dimethyl-3-(2,2,2-dibromo-1-methylsulfonyloxyethyl)-cyclopropane carboxylate Using the procedure of Step C of Example 6, the product of Step B was reacted to obtain 3-phenoxy-benzyl 1R-[1α-, 3α-(R)] 2,2-dimethyl-3-(2,2,2-dibromo-1-methylsulfonyloxyethyl)-cyclopropane carboxylate melting at 72° C.

EXAMPLE 8

(S)α-cyano-3-phenoxy-4-fluoro-benzyl 1R-[1α-(S) 3α-(R)] 2,2-dimethyl-3-[2,2,2-tribromo-1-methylsulfonyloxyethyl]-cyclopropane carboxylate STEP A: α-Cyano-3-phenoxy-4-fluoro-benzyl 1R-[1α-(S) 3α-(R) 3-[2,2,2-tribromo-1-trimethylsilyloxyethyl]-2,2-dimethyl-cyclopropane carboxylate Using the procedure of Example 7, 1R-[1α-, 3α-(R)] 2,2-dimethyl-3-[1-trimethylsilyloxy-2,2,2-tribromoethyl]-cyclopropane carboxylic acid and (S)α-cyano-3-phenoxy-4-fluoro-benzyl alcohol were reacted to obtain α-cyano-3-phenoxy-4-fluoro-benzyl 1R-[1α-(S) 3α-(R) 3-[2,2,2-tribromo-1-trimethylsilyloxyethyl]-2,2-dimethyl-cyclopropane carboxylate melting at 133° C.

STEP B: (S) α-Cyano-3-phenoxy-4-fluoro-benzyl 1R-[1α-(S) 3α-(R)] 3-[2,2,2-tribromo-1-hydroxyethyl]-2,2-dimethyl-cyclopropane carboxylate Using the procedure of Example 7 by hydrolysis of the product of Step A, there was obtained (S) α-cyano-3-phenoxy-4-fluoro-benzyl 1R-[1α-(S)3α-(R)] 3-[2,2,2-tribromo-1-hydroxyethyl]-2,2-dimethyl-cyclopropane carboxylate which was used as is in the next step.

STEP C: (S) α-Cyano-3-phenoxy-4-fluoro-benzyl 1R-[1α-(S) 3α-(R)] 2,2-dimethyl-3-[2,2,2-tribromo-1-methylsulfonyloxyethyl]-cyclopropane carboxylate Using the procedure of Example 7, the product of Step B and mesyl chloride were reacted to obtain α-cyano-3-phenoxy-4-fluoro-benzyl 1R-[1α-(S) 3α-(R)] 2,2-dimethyl-3-[2,2,2-tribromo-1-methylsulfonyloxyethyl]-cyclopropane carboxylate with a specific rotation of $[\alpha]_D^{20} = +34° \pm 1°$ (c=1% in CHCl$_3$)

EXAMPLE 9

α-Cyano-3-phenoxy-benzyl 1R-[1α-(S) 3α-(R)] 2,2-dimethyl-3-[2,2,2-tribromo-1-(2-propene-1-sulfonyloxy)ethyl]-cyclopropane carboxylate By esterifying the product of Example 1 with 1-sulfonyloxy-2-propenyl chloride, there was obtained α-cyano-3-phenoxy-benzyl 1R-[1α-(S) 3α-(R)] 2,2-dimethyl-3-[2,2,2-tribromo-1-(2-propene-1-sulfonyloxyethyl]-cyclopropane carboxylate melting at 96° C.

EXAMPLE 10

(S) α-Cyano-3-phenoxy-benzyl 1R-[1α-(S) 3α-(R)] 2,2-dimethyl-3-[2,2,2-tribromo-1-trifluoromethylcarbonyloxyethyl]-cyclopropane carboxylate STEP A: 1,1-dimethylethyl 1R-[1α, 3α-(R)] 2,2-dimethyl-3-[2,2,2-tribromo-1-trifluoromethylcarbonyloxyethyl]-cyclopropane carboxylate 16 ml of trifluoroacetic acid were added at 10° to 15° C. to a mixture of 5 g of tertbutyl 2,2-dimethyl-3-[2,2,2-tribromo-1-hydroxyethyl]-cyclopropane carboxylate and 20 ml of pyridine and the reaction mixture was allowed to return to 20° to 25° C. and was stirred for 90 minutes. The reaction mixture was poured into a mixture of water and ice and extraction was carried out with ether. The extracts were dried and evaporated to dryness under reduced pressure to obtain a residue which was cooled with hexane, dried and brought to dryness to obtain 5.09 g of 1,1-dimethylethyl 1R-[1α, 3α-(R)] 2,2-dimethyl-3-[2,2,2-tribromo-1-trifluoromethylcarbonyloxyethyl]-cyclopropane carboxylate melting at 102° C.

STEP B: 1R-[1α,3α-(R)]-2,2-dimethyl-3-[2,2,2-tribromo-1-trifluoromethylcarbonyloxyethyl]-cyclopropane carboxylic acid By hydrolysing the product obtained at Step A in benzene at reflux 1R-[1α,3α-(R)]-2,2-dimethyl-3-[2,2,2-tribromo-1-trifluoromethylcarbonyloxyethyl]-cyclopropane carboxylic acid melting at 178° C., is obtained.

STEP C: (S) α-Cyano-3-phenoxy-benzyl 1R-[1α-(S) 3α-(R)] 2,2-dimethyl-3-[2,2,2,-tribromo-1-trifluoromethylcarbonyloxyethyl]-cyclopropane carboxylate Using the procedure of Step B of Example 1, the acid of Step B and (S) α-cyano-3-phenoxy-benzyl alcohol were reacted to obtain (S) α-cyano-3-phenoxy-benzyl 1R-[1α-(S) 3α-(R)] 2,2-dimethyl-3-[2,2,2-tribromo-1-trifluoromethylcarbonyloxyethyl]-cyclopropane carboxylate melting at 79° C.

EXAMPLE 11

α-Cyano-3-phenoxy-benzyl 1R-[1α-(S) 3α-(R)] 2,2-dimethyl-3-[(1-diethoxyphosphoryloxy)-2,2,2-tribromoethyl]-cyclopropane carboxylate STEP A: Dimethylethyl 1R-[1α-, 3α-(R)]3-[2,2,2-tribromo-(diethoxyphosphoryloxy)-ethyl]-2,2-dimethyl-cyclopropane carboxylate 5.05 g of bromoform, 35 g of potassium tertbutylate and 20 ml of tetrahydrofuran were added at −60° C. to a suspension of 4 g of dimethylethyl keto [1α-, 3α-(R)]- cyclopropane carboxylate and 40 ml of tetrahydrofuran and the mixture was stirred for 15 minutes at −60° C. 3.6 g of diethoxyphosphoryloxy chloride were added and the mixture was stirred for one hour and a half at −60° C. and poured into a normal solution of hydrochloric acid. Extraction was carried out with ether and the extracts were washed with water, dried and evaporated to dryness under reduced pressure to obtain 7.09 g of dimethylethyl 1R-[1α-, 3α-(R) 3-[2,2,2-tribromo-(diethoxyphosphoryloxy)-ethyl]-2,2-dimethyl-cyclopropane carboxylate melting at 79° C.

STEP B: 1R-[1α-,3α-(R)] 3-[2,2,2-tribromo-1-diethoxyphosphoryloxy]-2,2-dimethyl-cyclopropane carboxylic acid A solution of 5 g of product of Step A, 50 ml of benzene and 0.5 g of p-toluene sulfonic acid was refluxed for one hour and the reaction mixture was cooled to 10° to 20° C. and poured into water. The organic phase was decanted, dried and evaporated to dryness under reduced pressure. The residue was taken up in hexane and the product obtained was separated to obtain 3 g of 1R-[1α-, 3α-(R)] 3-[2,2,2-tribromo-1-diethoxyphosphoryloxy]-2,2-dimethyl-cyclopropane carboxylic acid melting at 146° C.

STEP C: α-Cyano-3-phenoxy-benzyl 1R-[1α-(S) 3α-(R)] 2,2-dimethyl-3-[(1-diethoxyphosphoryloxy)-2,2,2-tribromoethyl]-cyclopropane carboxylate 1.22 g of cyclohexycarbodiimide and 5 ml of methylene chloride were added to a mixture of 3 g of acid of Step B, 1.34 g of (S) α-cyano-3-phenoxy-benzyl alcohol, 50 mg of 4-dimethylamino-pyridine and 30 ml of methylene chloride and the reaction mixture was allowed to return to ambient temperature and was maintained with stirring for one hour and a half. The product obtained was separated and brought to dryness, then chromatographed over silica, eluting with a hexane-ethyl acetate mixture (6-4) to obtain 3.3 g of α-cyano-3-phenoxy-benzyl 1R-[1α-(S) 3α-(R)] 2,2-dimethyl-3-[(1-diethoxyphosphoryloxy)-2,2,2-tribromoethyl]-cyclopropane carboxylate.

EXAMPLE 12

α-Cyano-3-phenoxy-benzyl 1R-[1α-(S) 3α-(R)] 3-[2,2,2-tribromo-1-(2-oxo-1,3,2-dioxaphospholanyloxy)-ethyl]-2,2-dimethyl-cyclopropane carboxylate

STEP A: 1,1-dimethylethyl 1R-[1α-, 3α-(R)] 3-[2,2,2-tribromo-1-(2-oxo-1,3,2-dioxaphospholanyloxy)-ethyl]-2,2-dimethyl-cyclopropane carboxylate 4.6 ml of bromoform were added at −60° C. to a solution of 9.9 g of 1,1-dimethylethyl 2,2-dimethyl-3-keto-(1R, 3α-) cyclopropane carboxylate in 100 ml of tetrahydrofuran and then 6.05 g of potassium tertbutylate and 50 ml of tetrahydrofuran were added at −60° C. Then, 7.5 g of 2-oxo-1,3,2-dioxophospholane chloride and 25 ml of tetrahydrofuran were added over 15 minutes at −60° C. and the mixture was stirred at −60° C. for 15 minutes, then poured into an aqueous solution of hydrochloric acid. The mixture was extracted with methylene chloride and the organic phases were washed with water, dried and evaporated to dryness under reduced pressure to obtain 27 g of residue which was triturated with 100 ml of ethyl ether. The product obtained was filtered and dried to obtain 18.4 g of 1,1-dimethylethyl 1R-[1α-, 3α-(R)] 3-[2,2,2-tribromo-1-(2-oxo-1,3,2-dioxaphospholanyloxy)-ethyl]-2,2-dimethyl-cyclopropane carboxylate melting at 210° C.

STEP B: 1R-[1α-, 3α-(R)] 3-[2,2,2-tribromo-1-(2-oxo-1,3,2-dioxaphospholanyloxy)-ethyl]-2,2-dimethyl-cyclopropane carboxylic acid 12.9 g of the product of Step A were added at reflux to a solution of 500 ml of benzne and p-tolune sulfonic acid and the mixture was refluxed for 30 minutes. The product obtained was brought to dryness, taken up in ethyl acetate, stirred for 15 minutes and filtered to obtain 5.5 g of 1R-[1α-, 3α-(R)] 3-[2,2,2-tribromo-1-2(2-oxo-1,3,2-dioxaphospholanyloxy)-ethyl-2,2-dimethyl-cyclopropane carboxylic acid melting at 225° C.

STEP C: (S) α-cyano-3-phenoxy-benzyl 1R-[1α-(S) 3α-(R)] 3-[2,2,2-tribromo-1-(1-oxo-1,3,2-oxaphospholanyloxy)-ethyl]-2,2-dimethyl-cyclopropane carboxylate Using the procedure of Example 1, Step B, 2.5 g of the product of Step B and 1.07 g of (S)α-cyano-3-phenoxy-benzyl alcohol were reacted to obtain (S)α-cyano-3-phenoxy-benzyl 1R-[1α-(S) 3α-(R)] 3-[2,2,2-tribromo-1-(2-oxo-1,3,2-oxaphospholanyloxy)-ethyl]-2,2-dimethyl-cyclopropane carboxylate melting at 155° C. and having a specific rotation of $[\alpha]_D^{20} = +42° \pm 1.5°$ (c=1% in $CHCl_3$).

EXAMPLE 13

2-Methyl-3-phenyl-benzyl 1R-[1α-, 3α-(R)] 3-[2,2,2-tribromo-1-(2-oxo-1,3,2-dioxaphospholanyloxy)-ethyl]-2,2-dimethyl-cyclopropane carboxylate The acid of Step B of Example 6 and [2-methyl-2-phenylphenyl]-methyl alcohol were reacted to obtain 2-methyl-3-phenyl-benzyl 1R-[1α-,3α-(R)] 3-[2,2,2-tribromo-1-(2-oxo-1,3,2-dioxaphospholanyloxy)-ethyl]-2,2-dimethyl-cyclopropane carboxylate melting at 182° C.

EXAMPLE 14

α-Cyano-3-phenoxy-benzyl 1R-[1α-(S) 3α-(R or S)] 3-[2,2,2-trichloro-1-(diethoxythiophosphoryloxy)-ethyl]-2,2-dimethyl-cyclopropanecarboxylate

STEP A: Dimethylethyl 1R-[1α, 3α-(R+S)] 3-[2,2,2-trichloro-1-(diethoxyphosphoryloxy)-ethyl] 2,2-dimethyl-cyclopropane carboxylate 0.84 ml of chloroform and 1.21 g of potassium tertbutylate in 10 ml of tetrahydrofuran were added at −60° C. to a solution of 1.98 g of 1,1-dimethylethyl 2,2-dimethyl-3-keto-(1α, 3α) -cyclopropane carboxylate in 10 ml of tetrahydrofuran and the mixture was stirred for 30 minutes at −60° C. and 1.88 g of 0,0-diethyl-chlorothiophosphate were added and the temperature was allowed to return to 20° to 25° C. Stirring was continued for 5 hours and the reaction mixture was poured into a normal solution of hydrochloric acid, and extracted with ether. The extracts were separated and evaporated to dryness under reduced pressure, then chromatographed over silica and eluted with a hexane-isopropyl ether mixture (9-1) to obtain 2.15 g of dimethylethyl 1R-[1α-, 3α-(R+S)] 3,-[2,2,2-trichloro-1-(diethoxyphosphoryloxy)-ethyl]-2,2-dimethyl-cyclopropane carboxylate.

STEP B: 1R-[1α-, 3α-(R+S)] 3-[2,2,2-trichloro-1-(diethoxythiophosphoryloxy)-ethyl]-2,2-dimethyl-cyclopropane carboxylic acid Using the procedure of Step B of the previous Example, the product of Step A was reacted to obtain 1R-[1α-, 3α-(R+S)] 3-[2,2,2-trichloro-1-(diethoxythiophosphoryloxy)-ethyl]-2,2-dimethyl-cyclopropane carboxylic acid.

STEP C: α-cyano-3-phenoxy-benzyl 1R-[1α-(S) 3α-(R or S)] 3-[2,2,2-trichloro-1-diethoxythiophosphoryloxy)-ethyl]-2,2-dimethyl-cyclopropane carboxylate Using the procedure of Step C of the previous Example, the product of Step B was reacted and the product obtained was chromatographed over silica and eluted with a hexane-ethyl acetate mixture (7-3) to obtain 0.850 g of isomer A of α-cyano-3-phenoxy-benzyl 1R-[1α-(S) 3α-(R or S)] 3-[2,2,2-trichloro-1-diethoxythiophosphoryloxy)-ethyl]-2,2-dimethyl-cyclopropane carboxylate.

NMR Spectrum: Paired $CH_3$ 73-4 Hz; H cyclopropyl 110 to 116 Hz; CH-13 O—P 312 to 342 Hz; CH— 402; Aromatics 416 to 457; and 0.800 g of product B.

NMR Spectrum: Paired $CH_3$ 73-75 Hz; —CH— 384 Hz; Aromatic 425 or 452 Hz; —CN.

EXAMPLE 15

α-Cyano-3-phenoxy-benzyl 1R-[1α-, 3α-(R)] 3-[2,2,2-trichloro-1-methylsulfonyloxyethyl]-2,2-dimethyl-cyclopropane carboxylate

STEP A: Dimethylethyl 1R-[1α-, 3α-(R)] 3-[2,2,2-trichloro-1-hydroxyethyl]-2,2-dimethyl-cyclopropane carboxylate With stirring under a nitrogen atmosphere, 2,2 ml of chloroform, then 2.95 g of potassium tertbutylene and 25 ml of tetrahydrofuran were added at −60° to −55° C. to a mixture of 4.95 g of tertbutyl 3-formyl-1R, 3R 2,2-dimethyl-cyclopropane carboxylate and 50 ml of tetrahydrofuran and the reaction mixture was stirred for 2 hours and 30 minutes. Extraction was carried out with ether and the organic phase was washed, dried and evaporated to dryness under reduced pressure. The product obtained was chromatographed by eluting with a hexane-ethyl acetate mixture (7-1) to obtain 6.45 of dimethyl ethyl 1R-[1α-, 3α-(R)] 3-[2,2,2-trichloro-1-hydroxy-ethyl]-2,2-dimethyl-cyclopropane carboxylate melting at 50° C.

STEP B: Dimethylethyl. 1R-[1α-, 3α-(R)] 3-[2,2,2-trichloro-1-methylsulfonyloxyethyl]-cyclopropane carboxylate 5.6 ml of triethylamine and 6 ml of tetrahydrofuran were added at 0° to 5° C. to a mixture of 6.35 g of the product of Step A, 65 ml of tetrahydrofuran and 3.2 ml of mesyl chloride and the reaction mixture was poured into water and extracted with ether. The extracts were dried on sodium sulfate, filtered and evaporated to dryness to obtain 8.1 g of dimethylethyl 1R-[1α-, 3α-(R)] 3-[2,2,2-trichloro-1-methyl sulfonyloxyethyl]-cyclopropane carboxylate melting at 106° C.

STEP C: 1R-[1α-, 3α-(R)] 3-[2,2,2-trichloro-1-methysulfonyloxyethyl-cyclopropane] carboxylic acid 6.5 g of the product of Step B, 65 ml of benzene and 150 mg of p-toluene sulfonic acid were refluxed for 1 hour and the reaction mixture was poured into water, extracted with methylene chloride and brought to dryness to obtain 5.15 g of crystals of 1R-[1α-, 3α-(R)] 3-[2,2,2-trichloro-1-methylsulfonyloxyethyl]-cyclopropane carboxylic acid melting at 148° C.

STEP D: α-Cyano-3-phenoxy-benzyl 1R-[1α-, 3α-(R)] 3-[2,2,2-trichloro-1-methylsulfonyloxyethyl]-2,2-dimethyl-cyclopropane carboxylate Using the procedure of Example 1, esterifying the acid obtained in the previous Step with (S)α-cyano 3-phenoxy-benzyl alcohol yielded α-cyano-3-phenoxy-benzyl 1R-[1α-, 3α-(R)] 3-[2,2,2-trichloro-1-methylsulfonyloxyethyl]-2,2-dimethyl-cyclopropane carboxylate with a specific rotation of $[\alpha]_D^{20} = +33° \pm 1°$ (c = 1% in $CHCl_3$).

EXAMPLE 16

(S)α-cyano-3-phenoxy-4-fluoro-benzyl 1R-[1α-(S) 3α-(R)] 3-[2,2,2-trichloro-1-methylsulfonyloxyethyl]-2,2-dimethyl-cyclopropane carboxylate The product was prepared by esterification of the acid of Step C of Example 15 with Sα-cyano-4-fluoro-3-phenoxy-benzyl alcohol and it had a specific rotation of $[\alpha]_D^{20} = +38° \pm 1°$ (c = 1.5% in $CHCl_3$)

EXAMPLE 17

α-Cyano 1-(6-phenoxy-2-pyridyl)-methyl 1R-[1α-, 3α-(R)] 3-[2,2,2-trichloro-1-methylsulfonyloxyethyl]-2,2-dimethyl-cyclopropane carboxylate The product was prepared by esterification of the acid of Step C of Example 15 with RS-cyano-1-(6-phenoxy-2-pyridyl)-methyl alcohol and it had a specific rotation of $[\alpha]_D^{20} = 2° \pm 1°$ (c = 0.8% in $CHCl_3$).

EXAMPLE 18

2-Methyl-3-phenyl-benzyl 1R-[1α-, 3α-(R)] 3-[2,2,2-trichloro-1-methylsulfonyloxyethyl]-cyclopropane carboxylate The product was prepared by esterification of the acid of Step C of Example 15 with 2-methyl-3-phenyl-benzyl alcohol and it had a specific rotation of $[\alpha]_D^{20} = 20° \pm 1°$ (c = 1% in $CHCl_3$)

EXAMPLE 19

α-Cyano-3-phenoxy-benzyl 1R-[1α-(S*) 3α-(R*)] 2,2-dimethyl 3-[2,2,2-trichloro-1-(4-methylphenylsulfonyloxyethyl]-cyclopropane carboxylate

STEP A: Dimethylethyl 1R-[1α,3α(R*)] 3-[2,2,2-trichloro-1-(4-methylphenylsulfonyloxy]-ethyl-2,2-dimethyl-cyclopropane carboxylate 1.7 ml of chloroform and then 2.42 g of potassium tertbutylate and 20 ml of tetrahydrofuran were added at −60° C. to a suspension of 3.96 g of tertbutyl (1R,3R) 3-formyl-cyclopropane carboxylate and 20 ml of tetrahydrofuran and stirring was carried out for 30 minutes at −60° C. 4 g of tosyl chloride and 10 ml of tetrahydrofuran were added over 15 minutes at −60° C. and the mixture was stirred for 30 minutes at −60° C. and then poured into 200 ml of a normal solution of hydrochloric acid. Extraction was carried out with ether and the extracts were washed, separated and evaporated to dryness under reduced pressure to obtain 5.3 g of dimethylethyl 1R-[1α,3α(R*)] 3-[2,2,2-trichloro-1-(4-methylphenylsulfonyloxy]-ethyl-2,2-dimethyl-cyclopropane carboxylate.

STEP B: 1R-[1α, 3α-(R*)] 3-[2,2,2-trichloro-1-(4-methylphenylsulfonyloxy)-ethyl]-2,2-dimethyl-cyclopropane carboxylic acid The ester of Step A was refluxed in benzene in the presence of p-toluene sulfonic acid to obtain 1R-[1α, 3α-(R*)] 3-[2,2,2-trichloro-1-(4-methylphenylsulfonyloxy)-ethyl]-2,2-dimethyl-cyclopropane carboxylic acid melting at 190° C.

STEP C: α-Cyano-3-phenoxy-benzyl 1R-[1α-(S*) 3α-(R*)] 2,2-dimethyl-3-[2,2,2-trichloro-1-(4-methylphenylsulfonyloxy)-ethyl]-cyclopropane carboxylate Esterification of the acid of Step B with S α-cyano-3-phenoxy-benzyl alcohol was carried out with procedure of Step C of Example 1 to obtain α-cyano-3-phenoxy-benzyl 1R-[1α-(S*) 3α-(R*)] 2,2-dimethyl-3-[2,2,2-trichloro-1-(4-methylphenylsulfonyloxy)-ethyl]-cyclopropane carboxylate with a specific rotation of $[\alpha]_D^{20} = 77.5° \pm 1.5°$ (c=1.1% in CHCl$_3$).

EXAMPLE 20

α-Cyano-3-phenoxy-benzyl 1R-[1α-(S) 3α-(S)] 2,2-dimethyl 3-[2,2,2-tribromo-1-methylsulfonyloxyethyl]-cyclopropane carboxylate

STEP A: 1,1-dimethylethyl 1R-[1α, 3α-(S)] 2,2-dimethyl 3-[2,2,2-tribromo-1-hydroxyethyl]-cyclopropane carboxylate 26 ml of bromoform were added to 39.6 g of 1,1-dimethylethyl 1R, 3R, 2,2-dimethyl-3-keto-cyclopropane carboxylate in solution in 200 ml of tetrahydrofuran and 17.5 g of potassium methylate, 100 ml of tertbutanol, 60 ml of tetrahydrofuran and 60 ml of dimethylformamide were added to the solution. The mixture was stirred for one hour at −10° C., then for one hour at +10° C. and then poured into water. Extraction was carried out with isopropyl ether and the extracts were dried and evaporated to dryness, under vacuum. The two diastereoisomers obtained were separated by chromatography.

STEP B: 1,1-dimethylethyl 1R-[1α, 3α-(S)] 2,2-dimethyl-3-[2,2,2-tribromo-1-methylsulfonyloxyethyl]-cyclopropane carboxylate A mixture of 4 g of the product of Step A, 40 ml of tetrahydrofuran and 2.03 g of mesyl chloride was cooled to 0°±5° C. and 1.78 g of triethylamine and 5 ml of tetrahydrofuran were added at 0°±5° C. The mixture was stirred for 2 hours at 0°±5° C. and then was poured into water, and extracted with methylene chloride. The extracts were dried and evaporated to dryness under reduced pressure and the residue was purified by crystallization from hexane, then from isopropyl ether to obtain 2.9 g of 1,1-dimethylethyl 1R-[1α, 3α-(S)]2,2-dimethyl-3-[2,2,2-tribromo-1-methylsulfonyloxyethyl-cyclopropane]carboxylate melting at 159° C.

STEP C: 1R-[1α, 3α-(S)] 2,2-dimethyl-3-2,2,2-tribromo-1-methylsulfonyloxyethyl]-cyclopropane carboxylic acid A mixture of 2.3 g of the product of Step B and 25 ml of benzene was refluxed and 70 mg of toluene sulfonic acid were added. The mixture was cooled, washed with water, dried and evaporated to dryness under reduced pressure to obtain 1.8 g of 1R-[1α, 3α-(S)]2,2-dimethyl-3-[2,2,2-tribromo-1-methylsulfonyloxyethyl]-cyclopropane carboxylic acid melting at 168° C.

STEP D: α-Cyano-3-phenoxy-benzyl 1R-[1α(S) 3α(S)]2,2-dimethyl-3-[2,2,2-tribromo-1-methylsulfonyloxyethyl]-cyclopropane carboxylate 0.78 g of dicyclohexylcarbodiimide and 3 ml of methylene chloride were added to a solution of 1.8 g of the product of Step C, 20 ml of methylene chloride, 0.85 g of (S) α-cyano-3-phenoxy-benzyl alcohol and 0.1 g of 4-dimethylamino-pyridine. The mixture was stirred at 20° to 25° C. for 2 hours and the product formed was dried and the filtrate was evaporated to dryness under reduced pressure. A chromatography was carried out with elution with a hexane-ethyl acetate mixture (7-3) to obtain 2 g of α-cyano-3-phenoxy-benzyl 1R-[1 α(S) 3α (S)] 2,2-dimethyl-3-[2,2,2-tribromo-1-methylsulfonyloxyethyl-cyclopropane]carboxylate with a specific rotation of $[\alpha]_D^{20} = 1° \pm 1°$ (c=1% in CHCl$_3$).

EXAMPLE 21

α-Cyano-3-phenoxy-benzyl [1R-[1α-S*, 3α-RS*, RS*] 2,2-dimethyl-3-[2-trifluoromethyl-2-bromo-2-chloro-1-methylsulfonyloxyethyl]-cyclopropane carboxylate

STEP A: 1,1-dimethylethyl[1R-[1α,3α-(RS*, RS*)]]2,2-dimethyl-3-[2-trifluoromethyl-2-bromo-2-chloro-1-hydroxyethyl]-cyclopropane carboxylate 3.1 g of potassium tertbutylate in 20 ml of THF were slowly added at −70° C. to a solution of 5 g of 1,1-dimethylethyl 1R,cis 2,2-dimethyl-3-formyl-cyclopropane carboxylate in 50 ml of THF and 3 ml of halothene (CF$_3$CHClBr). After a sufficient contact at this temperature, the medium was poured into a PO$_4$H$_2$Na aqueous solution and extraction was carried out with methylene chloride. The extracts were washed with water, and with a saturated solution of sodium chloride, dried and evaporated to dryness under reduced pressure. The product was chromatographed on silica and eluted with a hexane-isopropyl ether mixture (8-2) to obtain 6.83 g of 1,1-dimethylethyl[1R-[1α,3α-(RS*, RS*)]]2,2-dimethyl-3-[2-trifluoromethyl-2-bromo-2-chloro-1-hydroxyethyl]-cyclopropane carboxylate.

STEP B: 1,1-dimethylethyl [1R-[1α-,3α-(RS*RS*)]]2,2-dimethyl-3-[2-trifluoromethyl-2-bromo-2-chloro-1-methylsulfonyloxyethyl]-cyclopropane carboxylate 8 ml of triethylamine were added at −10° C. to a mixture of 6.74 g of the product of Step A, 40 ml of methylene chloride and 4.3 ml of mesyl chloride were added with stirring for one hour on an ice bath. After decanting, the organic phase was washed with water and with a saturated solution of sodium chloride, dried and evaporated to dryness under reduced pressure to obtain 9 g of product which was chromatographed on silica and eluted with a hexane-isopropyl ether mixture (8-2) to obtain 5.67 g of 1,1-dimethylethyl [1R-[1α-,3α-(RS*RS*)]] 2,2-dimethyl-3-[2-trifluoro methyl-2- bromo-2-chloro-1-methylsulfonyloxyethyl]-cyclopropane carboxylate melting at 100° C.

STEP C: [1R-[1α-,3α-(RS*,RS*)]]
2,2-dimethyl-3-[2-trifluoromethyl-2-bromo-2-chloro-1-methylsulfonylethyl]-cyclopropane carboxylic acid 30 mg of p-toluene sulfonic acid were added at 40° C. to a solution of 1 g of the product of Step B and 10 ml of methylene chloride and the reaction mixture was heated for 5 hours at 40° C., then poured on to ice, and decanted. The organic phase was washed with water, dried on sodium sulfate and evaporated to dryness under reduced pressure to obtain 860 mg of [1R-[1α-,3α-(RS*,RS*)]] 2,2-dimethyl-3-[2-trifluoromethyl-2-bromo-2-chloro-1-methylsulfonylethyl]-cyclopropane carboxylic acid melting at 138° C.

STEP D: (S) α-Cyano-3-phenoxy-benzyl [1R-[1α-(S*) 3α-(RS*,RS*)]]
2,2-dimethyl-3-[2-trifluoromethyl-2-bromo-2-chloro-1-methylsulfonyloxyethyl]-cyclopropane carboxylate Esterification of the acid of Step C with S α-cyano-3-phenoxybenzyl alcohol using the procedure of Step B of Example 1 yielded (S) α-cyano-3-phenoxy-benzyl [1R-[1α-(S*) 3α-(RS*,RS*)]] 2,2-dimethyl-3-[2-trifluoromethyl-2-bromo-2-chloro-1-methylsulfonyloxyethyl]-cyclopropane carboxylate.

NMR Spectrum (CDCl$_3$): Paired methyls=1.24–1.27 ppm and 1.22–1.27 ppm; H$_1$ and H$_3$=1.88 to 2.03 ppm; Ha=5.54 to 5.60 ppm; Hg=6.62 to 6.64 ppm; Aromatic H 6.99 to 7.42 ppm.

EXAMPLE 22

α-Cyano-3-phenoxy-4-fluoro-benzyl [1R-1α-(S*) 3α-(RS*,RS*)]]
2,2-dimethyl-3-[2-trifluoromethyl-2-bromo-2-chloro-1-methylsulfonyloxyethyl]-cyclopropane-carboxylate Using the procedure of Example 21, S α-cyano-4-fluoro-3-phenoxybenzyl alcohol and the appropriate acid were reacted to obtain α-cyano-3-phenoxy-4-fluoro-benzyl [1R-1α-(S*) 3α-(RS*,RS*)]] 2,2-dimethyl-3-[2-trifluoromethyl-2-bromo-2-chloro-1-methylsulfonyloxyethyl]-cyclopropane carboxylate.

NMR Spectrum (CDCl$_3$): Paired CH$_3$=1.23–1.25 ppm; H$_1$H$_3$=1.9–2.15 ppm; SO$_2$CH$_3$=3.1 ppm; H$_1'$=5.32–5.7 ppm; Benzyl H=6.5 ppm; Aromatic H=6.85 to 7.6 ppm.

EXAMPLE 23

α-Cyano-3-phenoxy 2-pyridyl-methyl [1R-[1α-(R,S*) 3α-(RS*)]]
2,2-dimethyl-[2-trifluoromethyl-2-bromo-2-chloro-1-methylsulfonyloxy-ethyl]-cyclopropane carboxylate Using the procedure of Example 21, RS α-cyano 1-(6-phenoxy-2-pyridy) methyl alcohol and the acid were reacted to obtain α-cyano-3-phenoxy 2-pyridyl-methyl [1R-[1α-(R,S*) 3α-(RS*)]] 2,2-dimethyl-[2-trifluoromethyl-2-bromo-2-chloro-1-methylsulfonyloxy-ethyl]-cyclopropane carboxylate.

NMR Spectrum CDCl$_3$: CH$_3$ methyl=1.25 1.3 1.43 ppm; H$_1$H$_3$=1.93 2.03 ppm; SO$_3$ CH$_3$=3.05–3.07 3.12–3.16 ppm; H$_1'$=5.32–5.7 ppm; Benzyl H=6.36–6.55 ppm; Aromatic H=6.87–7.99 ppm.

EXAMPLE 24

Pentafluoro-benzyl [1R-[1α-, 3α-RS*,RS*)]]
2,2-dimethyl-3-[2-trifluoromethyl-2-bromo-2-chloro-1-methyl sulfonyloxyethyl]-cyclopropane carboxylate Using the procedure of Example 21, pentafluorobenzyl alcohol was reacted to obtain pentafluoro-benzyl [1R-[1α-,3α-RS*,RS*)]] 2,2-dimethyl-3-[2-trifluoromethyl-2-bromo-2-chloro-1-methyl sulfonyloxyethyl]-cyclopropane carboxylate melting at 101° C.

NMR Spectrum CDCl$_3$: Paired CH$_3$=1.26–1.39 ppm; H$_1$, H$_3$=1.75–1.98 ppm; SO$_3$ CH$_3$=3.12–3.15 ppm; CO$_2$—CH$_2$=5.27 ppm; Ha=5.7 ppm.

EXAMPLE 25

2-methyl-3-phenyl-benzyl [1R-[1α-, 3α-(RS,RS)]]
2,2-dimethyl-3-[2-trifluoromethyl-2-bromo-2-chloro-1-methylsulfonyloxyethyl]-cyclopropane carboxylate Using the procedure of Example 21, 2-methyl-3-phenyl-benzyl alcohol was reacted to obtain 2-methyl-3-phenyl-benzyl [1R-[1α-, 3α-(RS,RS)]] 2,2-dimethyl-3-[2-trifluoromethyl-2-bromo-2-chloro-1-methylsulfonyloxyethyl]-cyclopropane carboxylate NMR Spectrum CDCl$_3$: Principal diastereoisomers (⅔); Paired CH$_3$=1.22–1.37 ppm; CH$_3$=2.22 ppm; CO$_2$ CH$_2$=5.27 ppm O$_2$S; CH$_3$ 3.04 ppm; Ha (5.6/5.64 ppm H$_1$; 1.8 to 2.06 ppm; (5.7 ppm H$_3$; Aromatic H=6.92/7.35 ppm.

EXAMPLE 26

3-phenoxy-benzyl [1R-[1α-, 3α-RS*,RS*)]]
2,2-dimethyl-3-[2-trifluoromethyl-2-bromo-2-chloro-1-methylsulfonyloxymethyl]-cyclopropane carboxylate STEP A: 3-phenoxy-benzyl [1R-[1α-, 3α-(RS*,RS*)]]
2,2-dimethyl-3-[2-trifluoromethyl-2-chloro-2-bromo-1-hydroxyethyl]-cyclopropane carboxylate Using the procedure of Step A of Example 21, 3-phenoxy-benzyl 1R, cis 2,2-dimethyl-3-formyl-cyclopropane carboxylate was reacted to obtain 3-phenoxy-benzyl [1R-[1α-, 3α-(RS*,RS*)]] 2,2-dimethyl-3-[2-trifluoromethyl-2-chloro-2-bromo-1-hydroxyethyl]-cyclopropane carboxylate.

NMR Spectrum CDCl$_3$: Paired CH$_3$=1.21 ppm; H$_1$ H$_3$=1.54 to 1.92 ppm; H$_1'$=4.28 ppm; CH$_2$=5.08 ppm; O H=3.22 ppm.

STEP B: 3-phenoxy-benzyl [1R-[1α-, 3α-(RS*,RS*)]]
2,2-dimethyl-3-[2-trifluoromethyl-2-bromo-2-chloro-1-methylsulfonyloxyethyl]-cyclopropane carboxylate Mesylation was carried out under the conditions of Step B of Example 21 to obtain 3-phenoxy-benzyl [1R-[1α-, 3α-(RS*,RS*)]] 2,2-dimethyl-3-[2-trifluoromethyl-2-bromo-2-chloro-1-methylsulfonyloxyethyl]-cyclopropane carboxylate.

NMR Spectrum CDCl$_3$: Paired CH$_3$=1.23/1.36 ppm; H$_1$ H$_3$=1.8 to 2.06 ppm; CH$_3$ SO$_2$=3.08/3.11 ppm; CO$_2$ CH$_2$=5.15 ppm; H$_1'$=3.85 ppm to 5.78 ppm; Aromatic H's, 6.87 to 7.55 ppm.

EXAMPLE 27

[1R-[1α-, 3α-]]
2,2-dimethyl-3-[2-trifluoromethyl-2-chloro-ethenyl]-cyclopropane carboxylic acid 2 g of 3-phenoxy-benzyl [1R-[1α-, 3α-(RS*,RS*)]] 2,2-dimethyl-3-[2-trifluoromethyl-2-bromo-2-chloro-1-methylsulfonyloxyethyl]-cyclopropane carboxylate were hydrogenated in 30 ml of ethanol in the presence of 200 mg of 10% palladium catalyst and filtration was carried out. The filtrate was evaporated to dryness under reduced pressure to obtain a residue which was dissolved in 20 ml of a normal sodium hydroxide solution. The aqueous phase was washed with methylene chloride, acidified with concentrated hydrochloric acid and extracted with methylene chloride. The extracts were dried and evaporated to dryness to obtain 400 mg of [1R-[1α-, 3α-]] 2,2-dimethyl-3-[2-trifluoromethyl-2-chloro-ethenyl]-cyclopropane carboxylic acid melting at 103° C.

NMR Spectrum CDCl₃: Isomer Z Ha=6.83 6.98 ppm; Isomer DE=6.55 6.7 ppm.

EXAMPLE 28

[2-methyl-(1,1'-biphenyl)-3-yl]-methyl 1R-[1α,3α-(RS*,RS*)] 2,2-dimethyl-3-[2-bromo-2-chloro-1-[4-methylphenyl-sulfonyloxy]-3,3,3-trifluoropropyl-cyclopropane carboxylate STEP A: [2-methyl-(1,1'-biphenyl)-3-yl]-methyl 1R (1α,3α)-2,2-dimethyl-3-formyl-cyclopropane carboxylate 0.55 g of sodium hydride were added slowly at 0° to 5° C. to a solution of 3.5 g of 1R (1α,3α) 2,2-dimethyl-3-formyl carboxylic acid in 100 ml of THF and after stirring for one hour at 0° C., 12.9 g of [2-methyl-(1,1'-biphenyl)-3-yl]-methyl bromide in 30 ml of dimethyl-formamide were added. Stirring was maintained for 22 hours at ambient temperature and part of the solvent was evaporated. The mixture was poured on to iced water and extracted with isopropyl ether. The organic phase was dried, evaporated to dryness and the residue was chromatographed on silica. (Eluent: hexaneisopropyl ether 7-3) to obtain 7.7 g of [2-methyl-(1,1'-biphenyl)-3-yl]-methyl 1R (1α,3α)-2,2-dimethyl-3-formyl-cyclopropane STEP B: [2-methyl-(1,1'-biphenyl)-3-yl]-methyl 1R-[1α,3α-(RS*,RS*)] 2,2-dimethyl-3-[2-bromo-2-chloro-1-[4-methylphenyl-sulfonyloxy]-3,3,3-trifluoropropyl-cyclopropane carboxylate 1.3 g of potassium tertbutylate dissolved in 10 ml of tetrahydrofuran were slowly added at −60° C. to 3.22 g of the product of Step A and 1.6 ml of halothane (CF₃CHBrCl) in solution in 15 ml of tetrahydrofuran. Then still at −60° C., 3.8 g of tosyl chloride and 0.8 g of 4-dimethylamino-pyridine in 20 ml of tetrahydrofuran were added. After 90 minutes of contact at −60° C., the reaction medium was poured into a solution of potassium mono phosphate and after extraction with methylene chloride, washing with water and drying of the organic phase and chromatography of the dry residue on silica (eluent: hexane-isopropyl ether 8-2), 3.5 g of pure [2-methyl-(1,1'-biphenyl)-3-yl]-methyl 1R[1,3-(RS*,RS*)] 2,2-dimethyl-3-[2-bromo-2-chloro-1-[4-methylphenylsulfonyloxy]-3,3,3-trifluoropropyl-cyclopropane carboxylate acid were isolated.

NMR Spectrum (CDCl₃: Paired CH₃=1.24-1.38 ppm; tosyl CH₃=2.4 ppm; CH₃=2.25 ppm; H₁H₃=1.83 to 2.1 ppm; H₁'=5.73-5.9 ppm.

EXAMPLE 29

α-Cyano-3-phenoxy-benzyl 1R-[1α-, 3α-(RS*,RS*)]] 3-[2-bromo-2-chloro-1-[diethoxyphosphonyloxy)] 3,3,3-trifluoropropyl-2,2-dimethyl-cyclopropane carboxylate STEP A: 1,1-dimethylethyl 1R (1α, 3α-(RS*,RS*) 3-(2-bromo-2-chloro-1-[diethoxy phosphonyloxy]-3,3,3-trifluoropropyl)-2,2-dimethyl-cyclopropane carboxylate 1.3 g of potassium tertbutylate dissolved in 10 ml of tetrahydrofuran were added slowly at −60° C. to a solution of 2 g of 1,1-dimethylethyl 1R (1α, 3α-) 3-formyl-2,2-dimethyl-cyclopropane carboxylate and 1.2 ml of halothane (CF₃CHBrCl) in 20 ml of tetrahydrofuran. After stirring for 15 minutes at −60° C., a solution of 1.6 ml of diethyl phosphate chloride in 4 ml of tetrahydrofuran was added dropwise. After 30 minutes of contact at −60° C., the mixture was poured into an aqueous solution of potassium mono phosphate. Extraction with methylene chloride yielded an oil which was purified by chromatography on silica to obtain 2.1 g of 1,1-dimethylethyl 1R (1α-, 3α-(RS*,RS*) 3-(2-bromo-2-chloro-1-[diathoxy phosphoryloxy]-3,3,3-trifluoropropyl)-2,2-dimethyl-cyclopropane carboxylate.

STEP B: α-Cyano-3-phenoxy-benzyl 1R-[1α-(S) 3α-(RS*,RS*)] 3-(2-bromo-2-chloro-1-diethoxyphosphonyloxy 3,3,3-trifluoropropyl)-2,2-dimethyl-cyclopropane carboxylate 1.74 g of the product of Step A were heated for 48 hours at reflux of 15 ml of benzene in the presence of 60 mg of p-toluene sulfonic acid. The reaction mixture was poured into a mixture of water and ice and extracted with methylene chloride. The extracts were washed, dried and concentrated to dryness. The residue was chromatographed over silica (eluent: hexane-ethyl acetate 1-1) and the intermediate acid was obtained. All of the acid was esterified with 0.46 g of S α-cyano-3-phenoxybenzyl alcohol made the conditions of Step B of Example 1. The purification by chromatography provided 0.6 g of α-cyano-3-phenoxy-benzyl. 1R-[1α-(S) 3α-(RS*,RS*)] 3-(2-bromo-2-chloro-1-diethoxy-phosphoryloxy 3,3,3-trifluoropropyl)-2,2-dimethyl-cyclopropane carboxylate.

NMR Spectrum (CDCl₃ Paired CH₃=1.17-1.23 ppm; CH₃ of EtO=1.36 ppm; CH₂ of EtO=4.17 ppm; H₁-H₃=1.93-1.96 ppm; H₁'=5.21 ppm; Benzyl H=6.55 ppm.

EXAMPLE 30

α-Cyano-3-phenoxy-benzyl 1R-[1α- (S) 3α- (R)] 2,2-dimethyl-3-[2,2,2-tribromo-1-[(3-hydroxy-2-methyl)-propylsulfonyloxy)-ethyl]-cyclopropane carboxylate 5 g of the product of Example 5 and 3.75 g of N-methylmorpholine-N-oxide in 125 ml of tetrahydrofuran and 40 ml of water were mixed together at ambient temperature. 100 mg of osmium tetroxide were added, and stirring was carried out for 22 hours at 20° C. The reaction medium was diluted with 250 ml of methylene chloride, cooled to 0° C. and then 6 g of sodium hydrosulfite in solution in 40 ml of water were added slowly. The mixture was allowed to return to ambient temperature, dried, and the solvents were eliminated under reduced pressure to obtain 5.1 g of crude product which was chromatographed on silica (eluent: hexane-ethyl acetate 85-15) to obtain 1.7 g of α-cyano-3-phenoxy-benzyl 1R-[1α- (S) 3α- (R)] 2,2-dimethyl-3-[2,2,2-tribromo-1-[(3-hydroxy-2-methyl)-propylsulfonyloxy)-ethyl]-cyclopropane carboxylate. Then after treatment with ether, 1.4 g of amorphous product with a specific rotation of $[\alpha]_D^{20} = +38° \pm 1°$ (c=1.% in chloroform) were obtained.

Analysis: $C_{26}H_{28}Br_3NO_8S$: molecular weight=754.306: Calculated: % C 41.40; % H 3.74; % N 1.86; % Br 31.78; % S 4.25; Found: % C 41.7; % H 3.7; % N 1.9; % Br 30.0; % S 4.1.

EXAMPLE 31

α-Cyano-3-phenoxy-benzyl 1R-[1α-(S) 3α-(R)] 2,2-dimethyl-3-[2,2,2-tribromo-1-[(3-hydroxy-2-hydroxy)-propylsulfonyloxy)-ethyl]-cyclopropane carboxylate Using the procedure of Example 30, the product of Example 9 was reacted to obtain after chromatography on silica (eluent: methylene chloride-ethyl acetate 1-1) and taking up the residue in either, 2.6 g of α-cyano-3-phenoxy-benzyl 1R-[1α-(S) 3α-(R)] 2,2-dimethyl-3-[2,2,2-tribromo-1-[(3-hydroxy-2-hydroxy)-propysulfonyloxy)-ethyl]-cyclopropane carboxylate with a specific rotation of $[\alpha]_D^{20} = +41° \pm 1.5°$ (c=0.7% in $CHCl_3$).

Analysis: $C_{25}H_{26}Br_3NO_8S$: molecular weight=754.306: Calculated: % C 40.56; % H 3.54; % N 1.89; % Br 32.38; % S 4.33; Found: % C 40.8; % H 3.3; % N 1.8; % Br 30.5; % S 4.3.

EXAMPLE 32

α-Cyano-3-phenoxy-benzyl 1R-[1α-(S) 3α-(R)] 2,2-dimethyl-3-[2,2,2-tribromo-1-[(2,2-dimethyl-3-dioxolan-4-yl)-methylsulfonyloxy)-ethyl]-cyclopropane carboxylate 1.3 g of the product of Example 31 and 130 mg of p-toluene sulfonic acid were stirred for 2 hours at 20° C. in 130 ml of acetone and then was diluted with 100 ml of water. After drying, the solvents were eliminated under reduced pressure to obtain 1.25 g of residue which was chromatographed over silica (eluent: hexane-ethyl acetate 3-1) to obtain 1.15 g of α-cyano-3-phenoxy-benzyl 1R-[1α-(S) 3α-(R)] 2,2-dimethyl-3-[2,2,2-tribromo-1-[(2,2-dimethyl-3-dioxolan-4-yl)-methylsulfonyloxy)-ethyl]-cyclopropane carboxylate with a specific rotation of $[\alpha]_D^{20} = +44° \pm 1.5°$ (c=1% in $CHCl_3$).

Using the procedure of the previous Examples, the following products were prepared:

EXAMPLE 33

(S) α-cyano-3-phenoxy-benzyl (1R,cis) 2,2-dimethyl-3-(2,2,2-tribromo-1-trimethylsilyloxyethyl)-cyclopropane carboxylate melting at 98° C. and having a specific rotation of $[\alpha]_D^{20} = +64° \pm 1°$ (c=2% in toluene).

EXAMPLE 34

α-Cyano-3-phenoxy-benzyl [1α-(S), 3α-(R)] 3-[2,2,2,-tribromo-1-(2-ethyl pyridinium-phosphate)-ethyl]-2,2-dimethyl-cyclopropane carboxylate with a specific rotation of $[\alpha]_D^{20} = 13° \pm 2°$ (c=0.65% in chloroform).

EXAMPLE 35

α-Cyano-3-phenoxy-benzyl [1α-(S), 3α-(R)] 3-[2,2,2-tribromo-1-(2-ethyl trimethylammonium phosphate)-ethyl]-2,2-dimethyl-cyclopropane carboxylate with a specific rotation of $[\alpha]_D^{20} = +14° \pm 1°$ (c=1% in chloroform).

EXAMPLE 36

3-phenoxy-benzyl (1R,cis) 2,2-dimethyl-3-(2,2,2-trichloro-1R-methoxyethyl)-cyclopropane carboxylate Analysis: $C_{22}H_{23}Cl_3O_4$; Calculated: % C 57.72; % H 5.06; % Cl 23.23. Found: % C 57.8; % H 5.1; % Cl 23.0.

EXAMPLE 37

(RS) α-cyano-3-phenoxy-benzyl (1R,cis) 2,2-dimethyl-3-[2,2,2-trichloro-1R-methoxyethyl]-cyclopropane carboxylate Analysis: $C_{23}H_{22}Cl_3NO_4$; Calculated: % C 57.22; % H 4.59; % Cl 22.03; % n 2.9. Found: % C 57.5; % H 4.7; % Cl 21.9; % n 2.8.

EXAMPLE 38

3-phenoxy-benzyl (1R,cis) 2,2-dimethyl-3-[2,2,2-trichloro-1R-acetyloxyethyl]-cyclopropane carboxylate Analysis: $C_{23}H_{23}Cl_3O_5$; Calculated: % C 56.87; % H 4.77; % Cl 21.89. Found: % C 56.9; % H 4.8; % Cl 21.7.

EXAMPLE 39

(R) or (S) α-cyano-3-phenoxy-benzyl (1R,cis) 2,2-dimethyl-3-[2,2,2-trichloro-1R-methanesulfonyloxyethyl]-cyclopropane carboxylate with a specific rotation of $[\alpha]_D^{20} = +7°$ (c=0.75% in benzene).

EXAMPLE 40

Preparation of a soluble concentrate

A homogeneous mixture was made of

| | |
|---|---|
| Product of Example 2 | 0.25 g |
| Piperonyl butoxide | 1.00 g |
| Tween 80 | 0.25 g |
| Topanol A | 0.1 g |
| Water | 98.4 g |

EXAMPLE 41

Preparation of an emulsifiable concentrate

The following are homogeneously mixed:

| | |
|---|---|
| Product of Example 3 | 0.015 g |
| Piperonyl butoxide | 0.5 g |
| Topanol A | 0.1 g |
| Tween 80 | 3.5 g |
| Xylene | 95.885 g |

EXAMPLE 42

Preparation of an emulsifiable concentrate

A homogeneous mixture was made of:

| | |
|---|---|
| Product of Example 8 | 1.5 g |
| Tween 80 | 20.00 g |
| Topanol A | 0.1 g |
| Xylene | 78.4 g |

EXAMPLE 43

Preparation of a fumigant composition

The following were mixed homogeneously:

| Product of Example 20 | 0.25 g |
|---|---|
| Tabu powder | 25.00 g |
| Cedar leaf powder | 40.00 g |
| Pinewood dust | 33.75 g |
| Brilliant green | 0.5 g |
| p-nitrophenol | 0.5 g |

EXAMPLE 44

Example of alimentary feed for animals

A feed containing the following was used as a balanced basic food: maize, dehydrated alfafa, wheat straw, palmetto cobe with molasses, urea, a vitamin-containing mineral seasoning. This feed contained at least 11% crude protein substances (of which 2.8% were contributed by urea), 2.5% fatty substances and at most 15% cellulose substances, 6% mineral substances and 13% humidity. The feed corresponded to 82 fodder units per 100 kilos and contained per 100 kilos 910,000 I.U.s. of vitamin A, 91,000 I.U.s of vitamin D3, 150 mg of vitamin E, 150 mg of vitamin C. 0.3 kg of the compound of Example 1 per 100 kg of total food were incorporated in this food.

EXAMPLE 45

Example of feed for animals

The same balanced basic feed was used as for Example 44 with 0.04 kg of the compound of Example 2 per 100 kg of total food incorporated into this food.

BIOLOGICAL STUDY

1) Study of the knock-down activity on the domestic fly

The insects tested were female domestic flies aged from 4 to 5 days and the operation was carried out by topical spraying of 1 microliter of acetone solution on the dorsal thorax of the insects by an Arnold micromanipulator. 50 flies were used per treatment and a mortality test was carried out 24 hours after treatment. The results obtained expressed in LD$_{50}$ or dose in nanograms per individual necessary to kill 50% of the insects are in the following Table

| Compound of Example | LD$_{50}$ in ng/insect |
|---|---|
| 2 | 1.7 |
| 3 | 2.7 |
| 4 | 8.7 |
| 8 | 1.3 |
| 20 | 2.3 |
| 21 | 1.1 |
| 22 | 0.9 |
| 30 | 5.7 |
| 31 | 5.2 |
| 32 | 4.5 |

Conclusion

The products of the invention are endowed with a very good knock-down effect on domestic flies.

2) Study of the activity of tarsal contact on the germanic cockroach

The insects tested were male germanic cockroaches (Blatella germanica) and the test was carried out by depositing an acetone solution of known concentration on the bottom of a Petri dish with a diameter of 2 ml. After drying, 20 male cockroaches per concentration were allowed to remain for 1 hour and then the insects were transferred to a clean medium and their mortality was checked after 24 hours, 48 hours, 3 and 5 days. The result expressed as a lethal concentration 50 (LC 50) in mg/m2 are reported in the following Table.

| Compound of Example | CL 50 in mg/m2 |
|---|---|
| 2 | 1.2 |
| 3 | 0.2 |
| 4 | 2 |
| 5 | 2.5 |
| 8 | 0.07 |
| 9 | 0.06 |
| 20 | 0.3 |
| 21 | 0.02 |
| 22 | 0.005 |
| 23 | 0.12 |
| 25 | 0.15 |
| 30 | 0.30 |
| 31 | 0.29 |
| 32 | 0.22 |

3) Study of the lethal effect on larvae of Spodoptera Littoralis

The tests were carried out by topical application of an acetone solution on the dorsal thorax of the larvae by an Arnold micromanipulator. 15 larvae were used per dose of product tested and the larvae used were larvae of the fourth larval stage, that is aged about 10 days when they were bred at 20° C. and 65% relative humidity. After treatment, the individual larva were placed on an artificial nutritive medium (Poitout, medium) and a mortality check was carried out 48 hours after treatment. The experimental results obtained are summarized in the following Table:

Study of the activity by topical application on larvae of *Spodoptera littoralis*
Test Results

| Compound of Example | LD$_{50}$ in ng/insect |
|---|---|
| 2 | 13 |
| 3 | 11 |
| 4 | 25 |
| 8 | 2.8 |
| 20 | 6.5 |
| 21 | 23.5 |
| 22 | 9 |
| 23 | 24 |
| 25 | 32 |

Various modifications of the products and methods of the invention may be made without departing from the spirit or scope thereof and it should be understood that the invention is intended to be limited only as defined in the appended claims.

What we claim is:

1. A process for the preparation of a compound of the formula

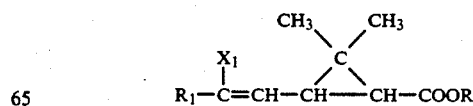

wherein $X_1$, $R_1$ and R have the following definitions comprising reacting a compound of the formula

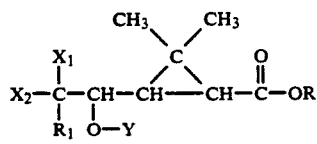

wherein $X_1$ and $X_2$ are individually halogen, $R_1$ is selected from the group consisting of halogen, alkyl of 1 to 8 carbon atoms, aryl of 6 to 14 carbon atoms, optionally substituted with at least one halogen perfluoroalkyl of 1 to 8 carbon atoms, —CN and

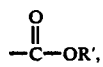

R' is alkyl of of 1 to 8 carbon atoms, Y is selected from the group consisting of —SO$_2$Alk$_1$, —SO$_2$Ar,

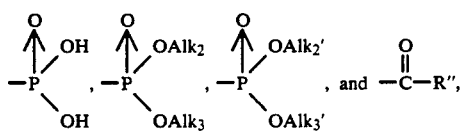

Alk$_1$ is optionally unsaturated alkyl of 1 to 8 carbon atoms, Ar is aryl of 6 to 14 carbon atoms optionally substituted or substituted with at least one halogen Alk$_2$ and Alk$_3$ and Alk$_2$ and Alk$_3$ are unsaturated alkyl of up to 8 carbon atoms or optionally substituted with at least one halogen or together with

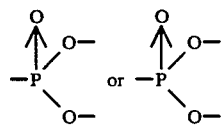

form the rings

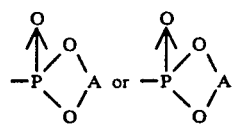

wherein. A is optionally unsaturated alkyl of up to 6 carbon atoms substituted with at least one halogen, R" is alkyl of up to 6 carbon atoms optionally substituted or unsubstituted with at least one halogen or aryl of 6 to 14 carbon atoms substituted with at least one halogen and R is selected from the group consisting of hydrogen, alkyl of 1 to 8 carbon atoms and residue of an alcohol used in pyrethrinoid esters with hydrogen in the presence of a palladium catalyst.

2. A process of claim 1 for the preparation of a compound of the formula

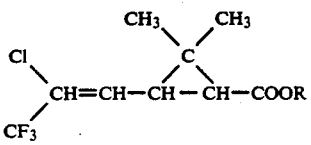

wherein R has the definitions of claim 1.

3. A process of claim 1 for the preparation of a compound of the formula

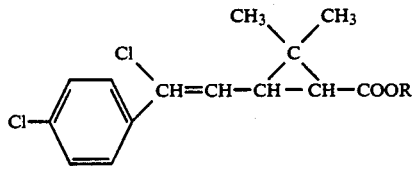

wherein R has the definitions of claim 1.

* * * * *